(12) United States Patent
Müller et al.

(10) Patent No.: US 10,940,122 B2
(45) Date of Patent: *Mar. 9, 2021

(54) TRANSDERMAL THERAPEUTIC SYSTEM WITH FENTANYL OR RELATED SUBSTANCES

(71) Applicant: LTS LOHMANN THERAPIE-SYSTEME AG, Andernach (DE)

(72) Inventors: Walter Müller, Andernach (DE); Thomas Hille, Neuwied (DE)

(73) Assignee: LTS LOHMANN THERAPIE-SYSTEME AG, Andernach (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/719,086

(22) Filed: Dec. 18, 2019

(65) Prior Publication Data

US 2020/0206148 A1 Jul. 2, 2020

Related U.S. Application Data

(63) Continuation of application No. 16/263,743, filed on Jan. 31, 2019, now Pat. No. 10,583,093, which is a continuation of application No. 10/487,393, filed as application No. PCT/EP02/07664 on Jul. 10, 2002, now Pat. No. 10,568,845.

(30) Foreign Application Priority Data

Aug. 24, 2001 (DE) .............................. 101 41 650.4

(51) Int. Cl.
  *A61K 9/70* (2006.01)
  *A61K 31/4468* (2006.01)

(52) U.S. Cl.
  CPC ........ *A61K 9/7061* (2013.01); *A61K 31/4468* (2013.01)

(58) Field of Classification Search
  CPC ... A61K 9/7061; A61K 31/4468; A61P 29/02; A61P 29/00; A61P 25/04
  See application file for complete search history.

(56) References Cited

U.S. PATENT DOCUMENTS

| | | |
|---|---|---|
| 2,618,708 A | 11/1952 | Ostline et al. |
| 2,884,126 A | 4/1959 | Ulrich et al. |
| RE24,906 E | 12/1960 | Ulrich |
| 3,886,126 A | 5/1975 | McKenna, Jr. et al. |
| 3,900,610 A | 8/1975 | McKenna, Jr. et al. |
| 4,053,604 A | 10/1977 | Jaramillo et al. |
| 4,486,423 A | 12/1984 | Kenyhercz |
| 4,508,715 A | 4/1985 | Booth et al. |
| 4,558,580 A | 12/1985 | Otty |
| 4,588,580 A | 5/1986 | Gale et al. |
| 4,599,342 A | 7/1986 | Lahann |
| 4,626,539 A | 12/1986 | Aungst et al. |
| 4,645,502 A | 2/1987 | Gale et al. |
| 4,758,434 A | 7/1988 | Kydonieus et al. |
| 4,822,802 A | 4/1989 | Levy et al. |
| 4,879,297 A | 11/1989 | Mahjour et al. |
| 4,906,463 A | 3/1990 | Cleary et al. |
| 4,911,707 A | 3/1990 | Heiber et al. |
| 4,911,916 A | 3/1990 | Cleary |
| 4,915,950 A | 4/1990 | Miranda et al. |
| 4,927,408 A | 5/1990 | Haak et al. |
| 4,938,759 A | 7/1990 | Enscore et al. |
| 5,000,886 A | 3/1991 | Lawter et al. |
| 5,080,646 A | 1/1992 | Theeuwes et al. |
| 5,120,532 A | 6/1992 | Wells et al. |
| 5,121,695 A | 6/1992 | Feuz |
| 5,122,127 A | 6/1992 | Stanley |
| 5,167,616 A | 12/1992 | Haak et al. |
| 5,180,716 A | 1/1993 | Yaksh et al. |
| 5,187,849 A | 2/1993 | Kobayashi |
| 5,203,768 A | 4/1993 | Haak et al. |
| 5,236,714 A | 8/1993 | Lee et al. |
| 5,254,346 A | 10/1993 | Tucker et al. |
| 5,260,066 A | 11/1993 | Wood et al. |
| 5,279,594 A | 1/1994 | Jackson |

(Continued)

FOREIGN PATENT DOCUMENTS

| | | |
|---|---|---|
| DE | 3526339 A1 | 1/1986 |
| DE | 4310012 A1 | 9/1994 |

(Continued)

OTHER PUBLICATIONS

Christen, H R., Introduction to Chemistry, 9th Edition (1974) pp. 53-55 (with English Translation).
U.S. Appl. No. 60/234,248, filed Sep. 19, 2000.
U.S. Appl. No. 60/236,973, filed Sep. 29, 2000.
U.S. Appl. No. 60/276,837, filed Mar. 16, 2001.
U.S. Appl. No. 60/284,017, filed Apr. 16, 2001.
Declaration of Dr. Walter Mueller (with English translation).
Declaration of Hyun Suk Yu, Feb. 2006.
DURO-TAK® Transdermal Grade Pressure Sensitive Adhesive, S.H. Steenhuis, National Starch & Chemical B.V., dated Feb. 2002.
DURO-TAK, Transdermal Grade Pressure Sensitive Adhesives, Product Selection Guide.

(Continued)

*Primary Examiner* — Hasan S Ahmed
(74) *Attorney, Agent, or Firm* — Sterne, Kessler, Goldstein & Fox P.L.L.C.; Matthew S. Bodenstein

(57) ABSTRACT

The invention relates to a transdermal therapeutic system (TTS), comprising a backing layer, which is permeable to the active ingredient, at least one matrix layer, comprising fentanyl or an active agent analogous to fentanyl, based on polyacrylate and a protective layer to be removed before usage, characterized in that the polyacrylate polymer is self-adhesive, free of carboxyl groups, has a saturation solubility for fentanyl of 3 to 20 wt. %, preferably of 4 to 12 and particularly of 5 to 10 wt. % and the layers contain at least 80% of the included active ingredient in a molecularly-dispersed, dissolved form.

17 Claims, No Drawings

(56) References Cited

U.S. PATENT DOCUMENTS

| | | |
|---|---|---|
| 5,288,497 A | 2/1994 | Stanley et al. |
| 5,288,498 A | 2/1994 | Stanley et al. |
| 5,405,997 A | 4/1995 | Hester, Jr. et al. |
| 5,416,191 A | 5/1995 | Cheronis et al. |
| 5,451,408 A | 9/1995 | Mezei et al. |
| 5,456,923 A | 10/1995 | Nakamichi et al. |
| 5,462,744 A | 10/1995 | Gupte et al. |
| 5,465,151 A | 11/1995 | Wybourne et al. |
| 5,474,783 A | 12/1995 | Miranda et al. |
| 5,482,965 A | 1/1996 | Rajadhyaksha |
| 5,497,763 A | 3/1996 | Lloyd et al. |
| 5,507,277 A | 4/1996 | Rubsamen et al. |
| 5,522,385 A | 6/1996 | Lloyd et al. |
| 5,543,407 A | 8/1996 | Guodong |
| 5,558,879 A | 9/1996 | Chen et al. |
| 5,562,607 A | 10/1996 | Gyory, Jr. |
| 5,569,450 A | 10/1996 | Duan et al. |
| 5,589,480 A | 12/1996 | Elkhoury et al. |
| 5,589,498 A | 12/1996 | Mohr et al. |
| 5,608,035 A | 3/1997 | Yanofsky et al. |
| 5,619,984 A | 4/1997 | Hodson et al. |
| 5,635,204 A | 6/1997 | Gevirtz et al. |
| 5,656,286 A | 8/1997 | Miranda et al. |
| 5,686,112 A | 11/1997 | Liedtke |
| 5,693,335 A | 12/1997 | Xia et al. |
| 5,697,896 A | 12/1997 | McNichols et al. |
| 5,714,162 A | 2/1998 | Muller |
| 5,730,999 A | 3/1998 | Lehmann et al. |
| 5,762,952 A | 6/1998 | Barnhart et al. |
| 5,769,778 A | 6/1998 | Abrams et al. |
| 5,770,222 A | 6/1998 | Unger et al. |
| 5,785,599 A | 7/1998 | Reik |
| 5,785,989 A | 7/1998 | Stanley et al. |
| 5,788,980 A | 8/1998 | Nabahi |
| 5,804,213 A | 9/1998 | Rolf |
| 5,820,876 A | 10/1998 | Hoffmann |
| 5,858,410 A | 1/1999 | Muller et al. |
| 5,861,149 A | 1/1999 | Ritter |
| 5,861,439 A | 1/1999 | Gyory, Jr. et al. |
| 5,871,460 A | 2/1999 | Phipps et al. |
| 5,880,132 A | 3/1999 | Hill |
| 5,885,564 A | 3/1999 | Zastrow et al. |
| 5,886,164 A | 3/1999 | Bird et al. |
| 5,891,842 A | 4/1999 | Kream |
| 5,910,301 A | 6/1999 | Farr et al. |
| 5,919,473 A | 7/1999 | Elkhoury |
| 5,932,227 A | 8/1999 | Higo et al. |
| 5,948,433 A | 9/1999 | Burton et al. |
| 5,958,379 A | 9/1999 | Regenold et al. |
| 5,958,446 A | 9/1999 | Miranda et al. |
| 5,976,547 A | 11/1999 | Archer |
| 5,980,927 A | 11/1999 | Nelson et al. |
| 5,985,317 A | 11/1999 | Venkateshwaran et al. |
| 5,993,849 A | 11/1999 | Assmus et al. |
| 5,998,434 A | 12/1999 | Mitch et al. |
| 6,004,566 A | 12/1999 | Friedman et al. |
| 6,004,577 A | 12/1999 | Murdock |
| 6,024,976 A | 2/2000 | Miranda et al. |
| 6,039,977 A | 3/2000 | Venkatraman et al. |
| 6,049,733 A | 4/2000 | Phipps et al. |
| 6,063,399 A | 5/2000 | Assmus et al. |
| 6,074,665 A | 6/2000 | Horstmann et al. |
| 6,093,419 A | 7/2000 | Rolf |
| 6,098,619 A | 8/2000 | Britto et al. |
| 6,139,866 A | 10/2000 | Chono et al. |
| 6,143,278 A | 11/2000 | Elkhoury |
| 6,163,720 A | 12/2000 | Gyory, Jr. et al. |
| 6,181,963 B1 | 1/2001 | Chin et al. |
| 6,210,394 B1 | 4/2001 | Demopulos et al. |
| 6,210,705 B1 | 4/2001 | Mantelle et al. |
| 6,214,378 B1 | 4/2001 | Tanida et al. |
| 6,219,576 B1 | 4/2001 | Gupta et al. |
| 6,221,377 B1 | 4/2001 | Meyer |
| 6,221,385 B1 | 4/2001 | Camu et al. |
| 6,246,904 B1 | 6/2001 | Murdock |
| 6,255,502 B1 | 7/2001 | Penkler et al. |
| 6,261,582 B1 | 7/2001 | Needham et al. |
| 6,264,981 B1 | 7/2001 | Zhang et al. |
| 6,267,984 B1 | 7/2001 | Beste et al. |
| 6,275,728 B1 | 8/2001 | Venkatraman et al. |
| 6,306,876 B1 | 10/2001 | Carson et al. |
| 6,310,072 B1 | 10/2001 | Smith et al. |
| 6,319,510 B1 | 11/2001 | Yates |
| 6,355,657 B1 | 3/2002 | Osborne |
| 6,375,978 B1 | 4/2002 | Kleiner et al. |
| 6,383,471 B1 | 5/2002 | Chen et al. |
| 6,425,892 B2 | 7/2002 | Southam et al. |
| 6,436,433 B1 | 8/2002 | Mueller |
| 6,464,688 B1 | 10/2002 | Harper et al. |
| 6,465,004 B1 | 10/2002 | Rossi-Montero et al. |
| 6,579,059 B2 | 6/2003 | Chen |
| 6,596,261 B1 | 7/2003 | Adjei et al. |
| 6,605,060 B1 | 8/2003 | O'Neil |
| 6,610,317 B2 | 8/2003 | Straub et al. |
| 6,669,953 B1 | 12/2003 | Kamiyama |
| 6,685,964 B1 | 2/2004 | Bartholomaeus et al. |
| 6,737,080 B1 | 5/2004 | Schumann |
| 6,791,003 B1 | 9/2004 | Choi et al. |
| 6,841,161 B1 | 1/2005 | Passmore et al. |
| 6,868,286 B1 | 3/2005 | Hille et al. |
| 6,881,208 B1 | 4/2005 | Phipps et al. |
| 7,001,609 B1 | 2/2006 | Matson et al. |
| 7,026,360 B1 | 4/2006 | Festo |
| 7,504,114 B1 | 3/2009 | Kurita et al. |
| 7,556,823 B2 | 7/2009 | Miller, II et al. |
| 7,700,122 B1 | 4/2010 | Kolesnikov et al. |
| 10,568,845 B2 * | 2/2020 | Muller ................. A61K 9/7061 |
| 10,583,093 B2 * | 3/2020 | Muller .................... A61P 29/00 |
| 2001/0006967 A1 | 7/2001 | Crain et al. |
| 2001/0011095 A1 | 8/2001 | Shuster et al. |
| 2001/0018072 A1 | 8/2001 | Unger |
| 2001/0018457 A1 | 8/2001 | Disanto et al. |
| 2001/0024658 A1 | 9/2001 | Chen et al. |
| 2001/0031787 A1 | 10/2001 | Hsu et al. |
| 2001/0033828 A1 | 10/2001 | Edwards et al. |
| 2001/0033858 A1 | 10/2001 | Zhang |
| 2001/0033865 A1 | 10/2001 | Oshlack et al. |
| 2001/0037104 A1 | 11/2001 | Zhang et al. |
| 2001/0039343 A1 | 11/2001 | Mulvihill et al. |
| 2001/0047005 A1 | 11/2001 | Farrar |
| 2001/0053777 A1 | 12/2001 | Brecht |
| 2002/0004063 A1 | 1/2002 | Zhang |
| 2002/0004066 A1 | 1/2002 | Stanley et al. |
| 2002/0004484 A1 | 1/2002 | Pasternak et al. |
| 2002/0010127 A1 | 1/2002 | Oshlack et al. |
| 2002/0012677 A1 | 1/2002 | Levine et al. |
| 2002/0017296 A1 | 2/2002 | Hickle |
| 2002/0019421 A1 | 2/2002 | Biberman |
| 2002/0019563 A1 | 2/2002 | Webber et al. |
| 2002/0022054 A1 | 2/2002 | Sawada et al. |
| 2002/0028235 A1 | 3/2002 | Reed et al. |
| 2002/0032581 A1 | 3/2002 | Reitberg |
| 2002/0037313 A1 | 3/2002 | Simon |
| 2002/0042587 A1 | 4/2002 | Murdock |
| 2002/0044966 A1 | 4/2002 | Bartholomaeus et al. |
| 2002/0045572 A1 | 4/2002 | Clemens |
| 2002/0045636 A1 | 4/2002 | Clemens |
| 2002/0052007 A1 | 5/2002 | Chang et al. |
| 2002/0052573 A1 | 5/2002 | Georgieff |
| 2002/0053093 A1 | 5/2002 | Barak et al. |
| 2002/0055496 A1 | 5/2002 | McCoy et al. |
| 2002/0055704 A1 | 5/2002 | Scott et al. |
| 2002/0058050 A1 | 5/2002 | Sackler et al. |
| 2002/0058068 A1 | 5/2002 | Houze et al. |
| 2002/0058608 A1 | 5/2002 | Cormier et al. |
| 2002/0058809 A1 | 5/2002 | Emmanuel et al. |
| 2002/0071809 A1 | 6/2002 | Pather et al. |
| 2002/0077285 A1 | 6/2002 | Pasternak et al. |
| 2002/0081333 A1 | 6/2002 | Oshlack et al. |
| 2002/0086343 A1 | 7/2002 | Cameron et al. |
| 2002/0086890 A1 | 7/2002 | Levin et al. |
| 2002/0087193 A1 | 7/2002 | Riddle et al. |
| 2002/0099013 A1 | 7/2002 | Piccariello et al. |
| 2002/0099049 A1 | 7/2002 | Burch et al. |

(56) References Cited

U.S. PATENT DOCUMENTS

| | | |
|---|---|---|
| 2002/0102280 A1 | 8/2002 | Anderson |
| 2002/0106329 A1 | 8/2002 | Leslie |
| 2002/0106407 A1 | 8/2002 | Coleman et al. |
| 2002/0107265 A1 | 8/2002 | Chen et al. |
| 2002/0119187 A1 | 8/2002 | Cantor et al. |
| 2002/0123489 A1 | 9/2002 | Baxter et al. |
| 2002/0124272 A1 | 9/2002 | Messing et al. |
| 2002/0128248 A1 | 9/2002 | Salvemini |
| 2002/0128591 A1 | 9/2002 | Kleiner et al. |
| 2002/0132794 A1 | 9/2002 | Lind et al. |
| 2002/0137761 A1 | 9/2002 | Crain et al. |
| 2002/0147197 A1 | 10/2002 | Newman et al. |
| 2002/0160043 A1 | 10/2002 | Coleman |
| 2002/0164290 A1 | 11/2002 | Stefely et al. |
| 2002/0165248 A1 | 11/2002 | Wimmer et al. |
| 2002/0176841 A1 | 11/2002 | Barker et al. |
| 2002/0176888 A1 | 11/2002 | Bartholomaeus et al. |
| 2002/0177232 A1 | 11/2002 | Melker et al. |
| 2002/0179758 A1 | 12/2002 | Reed et al. |
| 2002/0183722 A1 | 12/2002 | Harper et al. |
| 2002/0187996 A1 | 12/2002 | Dewey et al. |
| 2002/0195493 A1 | 12/2002 | Dell |
| 2002/0197324 A1 | 12/2002 | Watts et al. |
| 2002/0198484 A1 | 12/2002 | Young et al. |
| 2003/0004126 A1 | 1/2003 | Bountra et al. |
| 2003/0004177 A1 | 1/2003 | Kao et al. |
| 2003/0004554 A1 | 1/2003 | Riff et al. |
| 2003/0013689 A1 | 1/2003 | Helton et al. |
| 2003/0026829 A1 | 2/2003 | Venkatraman et al. |
| 2003/0027835 A1 | 2/2003 | Hamon et al. |
| 2003/0027936 A1 | 2/2003 | Murray et al. |
| 2003/0032001 A1 | 2/2003 | Broderick et al. |
| 2003/0032361 A1 | 2/2003 | Murasko et al. |
| 2003/0032947 A1 | 2/2003 | Harper et al. |
| 2003/0035775 A1 | 2/2003 | Klibanov |
| 2003/0035831 A1 | 2/2003 | Modi |
| 2003/0049300 A1 | 3/2003 | Terry |
| 2003/0064093 A1 | 4/2003 | Jordan |
| 2003/0088236 A1 | 5/2003 | Johnson et al. |
| 2003/0091620 A1 | 5/2003 | Fikstad et al. |
| 2003/0095992 A1 | 5/2003 | Erhardt |
| 2003/0100507 A1 | 5/2003 | Gulati |
| 2003/0119827 A1 | 6/2003 | Hickey et al. |
| 2003/0125343 A1 | 7/2003 | Gambacorti-Passerini et al. |
| 2003/0129219 A1 | 7/2003 | Hong et al. |
| 2003/0130203 A1 | 7/2003 | Christoph et al. |
| 2003/0138503 A1 | 7/2003 | Staniforth et al. |
| 2003/0139396 A1 | 7/2003 | Gibson |
| 2003/0139698 A1 | 7/2003 | Hyson |
| 2003/0166624 A1 | 9/2003 | Gale et al. |
| 2003/0170295 A1 | 9/2003 | Kim et al. |
| 2003/0187009 A1 | 10/2003 | Wentland |
| 2003/0190290 A1 | 10/2003 | Calvin |
| 2003/0199426 A1 | 10/2003 | Carrara et al. |
| 2003/0216413 A1 | 11/2003 | Root-Bernstein et al. |
| 2003/0220497 A1 | 11/2003 | Hung et al. |
| 2003/0229263 A1 | 12/2003 | Connors et al. |
| 2004/0023249 A1 | 2/2004 | Balch |
| 2004/0034059 A1 | 2/2004 | Grarup et al. |
| 2004/0034108 A1 | 2/2004 | Whittle |
| 2004/0037882 A1 | 2/2004 | Johnson et al. |
| 2004/0081685 A1 | 4/2004 | Wright |
| 2004/0092531 A1 | 5/2004 | Chizh et al. |
| 2004/0096491 A1 | 5/2004 | Tateishi et al. |
| 2004/0101482 A1 | 5/2004 | Sanders |
| 2004/0116352 A1 | 6/2004 | Chizh et al. |
| 2004/0121979 A1 | 6/2004 | Susilo |
| 2004/0131665 A1 | 7/2004 | Wepfer |
| 2004/0138461 A1 | 7/2004 | Mathew et al. |
| 2004/0146547 A1 | 7/2004 | Marcenyac et al. |
| 2004/0167060 A1 | 8/2004 | Wolpe et al. |
| 2004/0180080 A1 | 9/2004 | Furusawa et al. |
| 2004/0186417 A1 | 9/2004 | Phipps et al. |
| 2004/0208918 A1 | 10/2004 | Koch et al. |
| 2004/0213855 A1 | 10/2004 | Pettersson et al. |
| 2004/0234584 A1 | 11/2004 | Muller et al. |
| 2004/0241218 A1 | 12/2004 | Tavares et al. |
| 2004/0241219 A1 | 12/2004 | Hille et al. |
| 2004/0258753 A1 | 12/2004 | Demeester et al. |
| 2005/0009796 A1 | 1/2005 | Goodchild et al. |
| 2005/0019381 A1 | 1/2005 | Petereit et al. |
| 2005/0048104 A1 | 3/2005 | Venkatraman et al. |
| 2005/0081440 A1 | 4/2005 | Sauvage et al. |
| 2005/0085440 A1 | 4/2005 | Birch et al. |
| 2005/0087198 A1 | 4/2005 | Bruno-Raimondi et al. |
| 2005/0176790 A1 | 8/2005 | Bartholomaus et al. |
| 2005/0181032 A1 | 8/2005 | Wilkins et al. |
| 2005/0186141 A1 | 8/2005 | Gonda et al. |
| 2005/0208117 A1 | 9/2005 | Venkatraman et al. |
| 2005/0278195 A1 | 12/2005 | Getz |
| 2006/0040869 A1 | 2/2006 | Roberts et al. |
| 2006/0116662 A1 | 6/2006 | McNichols et al. |
| 2007/0184097 A1 | 8/2007 | Kurita et al. |
| 2008/0038330 A1 | 2/2008 | Fleischer et al. |
| 2009/0238886 A1 | 9/2009 | O'Mahony |
| 2009/0264855 A1 | 10/2009 | Phipps |

FOREIGN PATENT DOCUMENTS

| | | |
|---|---|---|
| DE | 4438989 A1 | 3/1996 |
| DE | 19527925 A1 | 2/1997 |
| DE | 19912477 A1 | 9/2000 |
| DE | 20220982 U1 | 11/2004 |
| DE | 20221397 U1 | 10/2005 |
| EP | 0483105 A1 | 4/1992 |
| EP | 0622075 A1 | 11/1994 |
| EP | 0842662 A1 | 5/1998 |
| EP | 0887075 A2 | 12/1998 |
| WO | WO-9415609 A1 | 7/1994 |
| WO | WO-9518603 A1 | 7/1995 |
| WO | WO-9608229 A2 | 3/1996 |
| WO | WO-9813035 A1 | 4/1998 |
| WO | WO-9813085 A1 | 4/1998 |
| WO | WO-9836740 A2 | 8/1998 |
| WO | WO-9902141 A1 | 1/1999 |
| WO | WO-0024386 A1 | 5/2000 |
| WO | WO-0041538 A2 | 7/2000 |
| WO | WO-0064418 A2 | 11/2000 |
| WO | WO-0074661 A2 | 12/2000 |
| WO | WO-0126705 A2 | 4/2001 |
| WO | WO-0224157 A2 | 3/2002 |
| WO | WO-0226217 A2 | 4/2002 |
| WO | WO-02074286 A1 | 9/2002 |

OTHER PUBLICATIONS

Duro-Tak® Transdermal Grade Pressure Sensitive Adhesives Product Selection Guide, National Starch & Chemical, dated Jul. 22, 2003.

Extract Communication From Cornelius, Bartenbach, Haesemann in Case No. 21018429/06 *LTS Lohmann Therapie-Systeme AG* v. *Novosis AG* dated Oct. 4, 2007 (with English translation).

False., et al., "Fentanyl", Rompp Lexikon, Georg Thieme Verlang, 1997.

Feldstein, M.M., et al., "Hydrophilic Polymeric Matrices for Enhanced Transdermal Drug Delivery," International Journal of Pharmaceutics, 131(2):229-242, Elsevier B.V (Apr. 1996).

Gelva Multipolymer Solution 737, Nov. 13, 2000.

Grond S., et al., "Clinical Pharmacokinetics of Transdermal Opioids: Focus on Transdermal Fentanyl," Clinical Pharmacokinetics, 38(1):59-89, part of Springer Science+Business Media, Switzerland (Jan. 2000).

Handbook of Pressure Sensitive Adhesives, 2nd Edition, 1982, pp. 400,401,414-417.

Internet printout of Nov. 2003, Solubility Calculator.

Jasti, B.R., et al., "A Novel Method for Determination of Drug Solubility in Polymeric Matrices," Journal of Pharmaceutical Sciences, 93(8):2135-2141, Elsevier, United States (Aug. 2004).

Klaffenbach and Becker, Determination of solubility of Fentanyl in polyacrylate copolymer DuroTak 87-4098, Study report dated Dec. 11, 2005, pp. 4-8.

(56) References Cited

OTHER PUBLICATIONS

Kokubo, T., et al., "Interaction Between Drugs and Pressure-sensitive Adhesives in Transdermal Therapeutic Systems," Pharmaceutical Research, 11(1):104-107, Kluwer Academic/Plenum Publishers, United States (Jan. 1994).
LABTEC GmbH, "Determiniation of Solubility of Fentanyl in Polyacrylates," Langenfeld, Germany, 2007 (Submitted in file history of EP 1418894).
Letter of National Starch to Johnson & Johnson Services, dated Jan. 12, 2005.
Liu, P., et al., "A novel method for measuring solubility of a drug in an adhesive", Pharmaceutical Research, 14:S317 (1997)—Presented at the AAPS Annual Meeting, Boston MA, Nov. 19.
Milker el al., "Vernelzung von Copolymcrcn auf Acrylatbasis", 1984, 9:85-91, Muenchener Klebstoff-und Veredelungsscminar, Munchen, Germany.
Milker et al., Vernetzung von Copolymerisaten auf Acrylatbasis, 3:29-32, Germany (1985).
Mueller, W., Determination of saturatio solubilities of Fentanyl in Gelva 737, Durotak 387-4287 and Durotak 387-2287, Test Report from LTS Lohmann Therapie-Systeme, dated Jun. 21, 2007 (with English translation).
National Starch & Chemical, "Acrylic Polymers for transdermal systems", Bridgewater, NJ, 1997.
National Starch & Chemical, "Transdermal Grade Pressure Sensitive Adhesives", Bridgewater, NJ, 1999.
National Starch and Chemical Company Solubility Calculator, National Starch & Chemical, Adhesives Division, dated 2003.
Novis, A.G., "Loslichkeit von Fentanyl Base im Polymer des Klebers Gelva 737", Jun. 15, 2007.
O Neil., et al., "Fentanyl," The Merck Index, Forteenth Edition, pp. 4001 (2006).
Otto Albrecht Neumtiller, ROMPPS Chemie-Lexikon, 1981, pp. 986-987.
Patent Abstracts of Japan, vol. 015, No. 001 (C-0793) and JP02255611.
Roy, S.D and Flynn, G.L., "Solubility and Related Physicochemical Properties of Narcotic Analgesics," Pharmaceutical Research, 5(9):580-586, Kluwer Academic/Plenum Publishers, United States (Sep. 1988).
Roy, S.D., et al., "Controlled Transdermal Delivery of Fentanyl: Characterizations of Pressure-Sensitive Adhesives for Matrix Patch Design," Journal of Pharmaceutical Sciences, 85(5):491-495, Elsevier, United States (May 1996).
Salman, N., Solubility of Fentanyl Base in the Polymer base of the Adhesive Durotak 87-4098, Confidential Experimal Report, Ancino AG dated Mar. 3, 2009, pp. 1-4 (with English translation).
Satas, D., "Acrylic Adhesives", Handbook of Pressure Sensitive Adhesive Technology, Satas & Associates, 2nd Edition (1989), pp. 397-456.
Tan, H.S and Pfister, W.R, "Pressure-sensitive Adhesives for Transdermal Drug Delivery Systems," Pharmaceutical Science & Technology Today, 2(2):60-69, Mercury Airfreight International [distributor], England (Feb. 1999).
Appeal Brief filed on Oct. 18, 2016 for U.S. Appl. No. 10/487,393, filed Feb. 20, 2004.
Patent Board Decision—Examiner Reversed mailed on Feb. 12, 2019 for U.S. Appl. No. 10/487,393, filed Feb. 20, 2004.
Reply Brief filed on Mar. 10, 2017 for U.S. Appl. No. 10/487,393, filed Feb. 20, 2004.
Confidential Letter of National Starch to Alza, dated Apr. 28, 2004.
Office Action dated May 18, 2016, in U.S. Appl. No. 10/487,393, inventor Muller, W., et al., filed Feb. 20, 2004, 11 pages.
Office Action dated Jan. 16, 2013, in U.S. Appl. No. 10/487,393, inventor Muller, W., et al., filed Feb. 20, 2004, 8 pages.
Office Action dated Aug. 16, 2011, in U.S. Appl. No. 10/487,393, inventor Muller, W., et al., filed Feb. 20, 2004, 8 pages.
Office Action dated Dec. 22, 2009, in U.S. Appl. No. 10/487,393, inventor Muller, W., et al., filed Feb. 20, 2004, 10 pages.
Office Action dated Apr. 6, 2009, in U.S. Appl. No. 10/487,393, inventor Muller, W., et al., filed Feb. 20, 2004, 14 pages.
Office Action dated Jun. 11, 2007, in U.S. Appl. No. 10/487,393, inventor Muller, W., et al., filed Feb. 20, 2004, 5 pages.
Office Action dated Oct. 11, 2013, in U.S. Appl. No. 10/487,393, inventor Muller, W., et al., filed Feb. 20, 2004, 11 pages.
Office Action dated Apr. 8, 2010, in U.S. Appl. No. 10/487,393, inventor Muller, W., et al., filed Feb. 20, 2004, 10 pages.
Office Action dated Dec. 31, 2007, in U.S. Appl. No. 10/487,393, inventor Muller, W., et al., filed Feb. 20, 2004, 9 pages.
Muller, W., "Determination of saturation solubilities of Fentanyl in Gelva 737, Durotak 387-4287 and Durotak 387-2287," Lohmann Therapy Systems, dated Jun. 21, 2007, 2 pages.
Salman, N., "Solubility of Fentanyl Base in the Polymer of Duro-Tak® Adhesive 87-4098," Acino AG, dated Mar. 3, 2009, 8 pages.
Muller, W., "Statement by Dr. Walter Muller," LTS signed May 25, 2014, 8 pages.
Rompp, "Solutions: Breakdown," retrieved from https://roempp.thieme.de/roempp4.0/do/data/RD-12-01485, edited by Rompp author, dated Dec. 8, 2014, 13 pages.
Study Report, "Saturation concentration Fentanyl; Determination of the saturation concentration of Fentanyl in acrylic adhesives," No. 2002326, valid from Oct. 14, 2014, 30 pages.
Wolff, H-M., et al., "Measurement of the Saturation Solubility of Fentanyl in a Polyacrylate," LTS, dated Sep. 29, 2017, 45 pages.
Thieme Rompp, "Fentanyl," retrieved from https://roempp.thieme.de/roempp4.0/do/data/RD-0600480, dated Aug. 16, 2017, 11 pages.
German Patent and Trademark Office, "Oral Proceeding Rulings in the utility model cancellation action of model No. 202 21 087," dated Feb. 28, 2007, Munich, Germany, 17 pages.
German Patent and Trademark Office, "Oral Proceeding Rulings in the utility model cancellation action of model No. 202 21 160," Sep. 5, 2007, Munich, Germany, 16 pages.
German Patent and Trademark Office, "Oral Proceeding Rulings in the utility model cancellation action of model No. 202 21 161," Sep. 5, 2007, Munich, Germany, 15 pages.
Letter to the Patent Litigation Chamber, Munich District Court, "Reference No. 21 O 18429/06," Dated Feb. 2, 2007, 14 pages.
Letter to the Patent Litigation Chamber, Munich District Court, "Claim by LTS Lohmann Therapie-Systeme AG," Dated Oct. 11, 2006, 42 pages.
Prescribing Information, "Fentadolon Matrixpflaster," last updated Jan. 2007, 10 pages.
Novosis AG., "Solubility of Fentanyl Base in Polymer of the Gelva 737 Adhesive," dated Jun. 15, 2007, 8 pages.
Lohman Therapy Systems, "Determination of saturation solubilites of Fentanyl in Gelva 737, Durotak 387-4287 and Durotak 387-2287," Dated Jun. 21, 2007, 2 pages.
Antonietti, M., "Letter to Dr. Best," Dated Jan. 20, 2005, 14 pages.
Claims submitted Mar. 20, 2007, in European Patent Opposition EP1418894, signed Feb. 13, 2017, 5 pages.
Federal Patent Court, "Concerning the German Patent 101 41 650," reference No. 3 Ni 22/04, Dated Aug. 2005, 68 pages.
Test Report for EP 1 418 894 B1, dated Apr. 16, 2009, 9 pages.
Certified Korean Patent Application Priority Document No. 1999 43794. Date of Application Oct. 11, 1999, 57 pages.

* cited by examiner

TRANSDERMAL THERAPEUTIC SYSTEM WITH FENTANYL OR RELATED SUBSTANCES

Fentanyl and fentanyl-analogous substances such as sulfentanyl, carfentanyl, lofentanyl and alfentanyl are extremely efficacious analgesics. The requirement for only a low dose and their physicochemical properties such as the n-octanol/water partition coefficient, melting point and the molecular weight make possible the transdermal administration of these substances in an efficacious amount and their pharmacokinetic properties such as the rapid metabolization and the relatively narrow therapeutic index make transdermal administration desirable.

In fact, a TTS containing fentanyl as active compound has been on the market for some years. This system is a "reservoir system". A reservoir system is understood here as meaning a system which contains the active compound in a liquid or gelatinous preparation in a sachet formed from an impermeable film, which serves as a back layer, and an active compound-permeable membrane, the membrane additionally being provided with an adhesive layer for fixing the system to the skin. In this specific case, fentanyl is dissolved in a mixture of ethanol and water. Further details of this system can be taken from US patent specification 4,588,580 or DE-C 35 26 339, which both contain a detailed description.

Reservoir systems, however, have the disadvantage that in the case of a leak in the reservoir sachet the active compound-containing reservoir filling comes in contact with the skin over a wide area and the active compound is absorbed in excessively high doses. This is very dangerous, especially in the case of fentanyl and its derivatives, since an overdose very rapidly leads to respiratory depression and therefore fatal incidents. A number of such fatal or near-fatal incidents are described in *Clinical Pharmacokinet.* 2000, 38(1), 59-89.

The object of this invention was now to make available a transdermal therapeutic system containing fentanyl or fentanyl analogs, which offers the user increased safety against an inadvertent absorption of overdoses.

This is possible according to the invention in that, instead of the reservoir system, a matrix system is employed in which the active compound is incorporated directly into a self-adhesive polyacrylate and thus, even in the case of damage to the system, cannot come into contact with the skin over a greater area than afforded by the TTS. In such a system, the active compound is generally completely, but to at least 80%, dissolved in molecularly disperse form in this polymer, the saturation solubility of the active compound in the polymer being between 3 and 20% by weight. Furthermore, it has surprisingly been shown that when using polyacrylate adhesives for the production of TTS containing fentanyl and its analogs, only adhesives without free carboxyl groups are suitable.

Such matrix systems in the simplest case consist of a back layer, which is impermeable to the active compound, of a self-adhesive active compound-containing layer and of a protective layer to be removed before use. In complicated embodiments of such systems is additionally also added a membrane controlling the release of active compound, which is normally further provided with an adhesive layer for fixing the system to the skin.

The active compound-containing layers of such a matrix system according to this invention consist of polyacrylates. Since free functional groups increase the saturation solubility of fentanyl and its derivatives in polyacrylate adhesives above the preferred range, the polyacrylate adhesives which are best suited are those which have no free functional groups and are only prepared from esters of acrylic and/or methaycrylic acid and optionally other vinyl compounds without free functional groups such as vinyl acetate. However, in the synthesis of the adhesive, monomers having free hydroxyl groups such as 2-hydroxyethyl acrylate or 2-hydroxyethyl methacrylate can be tolerated up to a content of 20% by weight. Polyacrylates are prepared by free-radical polymerization using acrylic and/or methacrylic acid derivatives. Such derivatives are, for example, esters. By way of example of such derivatives, acrylic and methacrylic acid derivatives may be mentioned, in particular esters of alcohols having 1 to 8 C atoms, which optionally contain one hydroxyl group, such as 2-ethylhexyl acrylate, n-octyl acrylate, propyl acrylate, n- or isobutyl acrylate, 2-hydroxyethyl acrylate and dimethylaminoethyl acrylate or the corresponding methacrylates. Additionally, other polymerizable vinyl compounds without free functional groups such as, for example, vinyl acetate can also be used, e.g. in amounts of up to 50% by weight. The polymers thus prepared are also described as random copolymers, as solely the quantitative distribution of the monomers employed and chance decide the composition of the polymer chains.

If the polymers contain free hydroxyl groups, the possibility exists of additionally crosslinking the polymer chains by polyvalent cations such as $Al^{3+}$ or $Ti^{4+}$ or reactive substances such as melamine. Use is made of this possibility in order to increase the molecular weight and thus to improve the cohesion of the polymers. The possibility of the crosslinkage of polyacrylates, in particular of polyacrylate adhesives, is particularly valuable if the plasticizing action of the active compound dissolved in the polymers or the plasticizing action of other auxiliaries has to be compensated. The adhesive is usually used in the form of a solution. Solvents used are, for example, ethyl acetate, hexane or heptane, ethanol or their mixtures. These are removed during the preparation of the TTS.

Table 1 shows the results of permeation studies which have been obtained using an adhesive with and an adhesive without free carboxyl groups (but without hydroxyl groups). In both adhesives, the active compound was incorporated in a concentration of 5 percent by weight. The permeation study was carried out by means of the Franz diffusion cells known to the person skilled in the art and using human skin.

TABLE 1

Results of permeation studies using adhesives with and without free carboxyl groups

| Formulation | Cumulated amount of permeated active compound [µg/cm$^2$] Mean value of n = 3 * | | | | |
|---|---|---|---|---|---|
| | 4 h | 8 h | 24 h | 48 h | 72 h |
| 1 | 0.00 | 0.00 | 0.44 | 1.71 | 3.51 |
| 2 | 0.0 | 0.2 | 4.0 | 14.7 | 28.24 |

* skin used: female lower abdominal skin
Formulation 1: polyacrylate adhesive with 4.8% by weight of free carboxyl groups
Formulation 2: neutral polyacrylate adhesive without free carboxyl groups but with 5.2% by weight of free hydroxyl groups The results show that a neutral adhesive without free carboxyl groups is markedly superior to a carboxyl group-containing adhesive with respect to the permeation rates achievable.

An important characteristic of each active compound-containing polymer in TTS technology is the saturation solubility of the chosen polymer for the respective active compound. This parameter is important because the thermodynamic activity of the active compound in the matrix does not depend on the absolute amount of active compound dissolved, but rather on the ratio of the actual concentration to the saturation concentration. Since the active compound on application of the TTS to the skin must disperse in the skin and in the process bring into line not concentrations, but activities, it is important for achieving a permeation rate which is as high as possible to choose as high as possible a thermodynamic activity of the active compound in the TTS. This means that the solubility of the active compound in the active compound-containing parts of the TTS must not be too high, since otherwise the active compound concentration in the TTS must be quite high in order to achieve an adequately high thermodynamic activity. This is unadvantageous if the active compound disadvantageously influences the physical properties of the active compound-containing parts of the system in the high concentration and/or the active compound is very expensive. In the case of fentanyl, both reasons are true, it additionally still having to be taken into consideration that fentanyl and its derivatives belong to the narcotics and for this reason alone it is therefore desirable to incorporate as little active compound in the TTS as possible and/or to make the utilization of active compound, i.e. the ratio of active compound released during the wearing time of the TTS to the content of the unworn TTS, as large as possible.

From this point of view, the saturation solubility of the active compound-containing layers for a three-day TTS should not be below 3 percent by weight and not above 20 percent by weight. At higher saturation solubilities, even with a high specific permeation rate, the utilization of active compound is too poor, and the TTS is not readily marketable for commercial reasons because of the expensive active compound. Preferably, for these reasons the saturation solubility is between 4 and 12 and particularly preferably between 5 and 10, percent by weight.

The saturation solubility of fentanyl and its analogs can additionally be reduced by the addition of substances which do not have good dissolving properties for the active compound. Such substances are, for example, liquid hydrocarbons such as dioctylcyclo-hexane, liquid paraffin, hydrocarbon resins such as polyterpenes, in particular polypinene, or polar substances such as glycerol, di- and triglycerol or polyethylene glycols, e.g. having a molecular weight from 200 to 1000. These substances can form a homogeneous mixture with the polyacrylate adhesive or else be contained therein as a separate phase. Glycerol and its derivatives especially are already present in low concentrations in the matrix as a separate phase, e.g. in the form of droplets. By means of the addition of such substances, it is in particular also possible to compensate the higher saturation solubility in adhesives having free hydroxyl groups.

Table 2 contains some data regarding the saturation solubilities of fentanyl in some of these substances.

TABLE 2

Saturation solubilities of fentanyl in solubility-decreasing additives

| Substance | Saturation solubility [% by weight] |
|---|---|
| Polyethylene glycol 400 | 7.5 |
| Glycerol | <1.5 |
| Diglycerol | <1.5 |

TABLE 2-continued

Saturation solubilities of fentanyl in solubility-decreasing additives

| Substance | Saturation solubility [% by weight] |
|---|---|
| Dioctylcyclohexane | <1.9 |
| Paraffin, liquid | <1.5 |

The influence of such additives can be recognized by means of comparative permeation studies.

In table 3, the results of permeation studies with matrices based on a neutral polyacrylate adhesive having free hydroxyl groups with and without such additives and of a polyacrylate adhesive without other free functional groups are compared. All formulations contain fentanyl in a concentration of 5% by weight.

TABLE 3

Comparative permeation studies using formulations with and without solubility-decreasing additives

| | Cumulated amount of permeated active compound [µg/cm$^2$] Mean value of n = 3 * | | | | |
|---|---|---|---|---|---|
| Formulation | 4 h | 8 h | 24 h | 48 h | 72 h |
| 2 | 0.00 | 0.23 | 7.89 | 32.82 | 64.17 |
| 3 | 0.798 | 4.46 | 29.6 | 68.9 | 103.1 |
| 4 | 0.805 | 4.87 | 32.6 | 74.7 | 113.2 |

| Formulation 2: | 5% by weight fentanyl in a neutral polyacrylate adhesive with 5.2% free hydroxyl groups | |
|---|---|---|
| Formulation 3: | fentanyl | 5.0% |
| | polyacrylate adhesive, neutral with 5.2% free hydroxyl groups | 55.0% |
| | polypinene | 15.0% |
| | glycerol | 10.0% |
| | dioctylcyclohexane | 15.0% |
| Formulation 4: | 5% by weight of fentanyl in a polyacrylate adhesive without free functional groups | |

* skin: human epidermis, female breast skin

The results of the permeation study show that the permeation rate can be significantly improved by the addition of substances reducing the solubility of the active compound in the matrix. Approximately the same results are achieved by the use of an adhesive without free functional groups, which even without additives has a low dissolving capacity for the active compound.

From the permeation data, the respective TTS sizes can be calculated for various TTS strengths. The results are listed in table 4.

TABLE 4

TTS sizes calculated from permeation data

| | Calculated area sizes [cm$^2$] | | | | |
|---|---|---|---|---|---|
| Release rate | Form. 1 | Form. 2* | Form. 2** | Form. 3 | Form. 4 |
| 25 µm/h | 513 | 63.7 | 28.1 | 17.45 | 15.9 |
| 50 µm/h | 1026 | 127.4 | 56.2 | 34.9 | 31.8 |
| 75 µm/h | 1539 | 191.1 | 84.3 | 52.35 | 47.7 |
| 100 µm/h | 2052 | 254.8 | 112.4 | 69.8 | 63.6 |

*calculated on the basis of the permeation data from table 1
**calculated on the basis of the permeation date from table 2

The result of the calculation shows that carboxyl group-containing adhesives at a fentanyl concentration of 5% even at the lowest dose lead to TTS which are too large for practical use. Although quite large TTS are also calculated in the case of the hydroxyl group-containing adhesives, the possibility exists here due to the increase in the fentanyl concentration to arrive at TTS having a size suitable for practical use with concentrations which are not too high, i.e. at most 20%. Simplified, it can be assumed here that the thermodynamic activity and thus also the permeation rates depend linearly on the concentration, as long as the active compound is present completely dissolved.

By use of the solubility-lowering auxiliaries in formulations having hydroxyl group-containing polyacrylate adhesives or by the use of polyacrylate adhesives without free functional groups, even at a fentanyl concentration of 5%, TTS are obtained which have an acceptable size, even in the highest dose of 100 µg/h. Of course, the possibility also offers itself here of further reducing the system area by increasing the fentanyl concentration.

Fentanyl and its derivatives, as already mentioned at the outset, have a narrow therapeutic index. This means that for the action, on the one hand, a certain threshold value which must be exceeded with respect to the plasma concentration, on the other hand unacceptable side-effects rapidly occur at higher concentrations. It is therefore advantageous if the system additionally contains a control membrane and thus the active compound flow through the skin is restricted to a maximum value independently of the individual skin condition. Such membranes preferably consist of a copolymer of ethylene and vinyl acetate (EVA polymer) or are microporous films based on polyethylene or polypropylene. The prior art includes membranes of this type. In the case of the EVA polymers, the active compound permeability depends on the content of vinyl acetate and the thickness of the membrane. Membranes having a VA content of between 2 and 25 percent by weight and a thickness of between 25 and 100 µm, preferably between 40 and 100 µm, are customary, there being scarcely any limitations in practice with respect to the vinyl acetate content and the thickness. For the particular formulation, both parameters must be chosen accordingly in order to guarantee restriction to the desired maximum flow from the TTS. In the case of the microporous membranes, the substance transport does not take place through the polymer, but only through the pores found in these membranes. The number and size of the pores in this case determines the maximum release rate of the TTS.

Customarily, such membranes are provided with an adhesive film for fixing the TTS to the skin. Adhesive films based on self-adhesive polyacrylates or self-adhesive polysiloxanes are particularly suitable for fentanyl and its derivatives. The advantage of poly-siloxanes here is that the active compound in these polymers is very poorly soluble and therefore the active compound loading of the TTS does not have to be increased unnecessarily by the use of an additional adhesive film. Adhesive films of this type, however, can also be used in systems which contain no membranes, but matrix layers having lower adhesive power.

As in any TTS, of course, there is also the possibility here of reducing the barrier properties of the human horny layer by the use of permeation-promoting substances. Such substances are, for example, fatty acids, fatty alcohols, fatty acid esters, esters of glycerol with medium- or long-chain fatty acids and glycols such as 1,2-propanediol. All substances can be employed here which are physiologically acceptable and compatible with the active compound and the other excipients.

In summary, it is to be observed the matrix systems within the meaning of this invention show satisfactory to good permeation rates and also make possible the production of TTS having an acceptable size. At the same time, an endangering of the patient by an excessively high absorption of active compound as a result of a leak is impossible. Overall, matrix systems based on polyacrylate adhesives within the meaning of this invention are thus an important advance in relation to the known prior art for fentanyl and its analogs with respect to patient safety.

EXAMPLES

Example 1 (Formulation 1, 2, 4)

Fentanyl (free base) is dissolved in the solution of the adhesive in heptane/ethyl acetate. The amount of fentanyl is in this case calculated such that, based on the solids content of the adhesive solution, a concentration of 5.0% results. The resulting material is coated using a doctor blade onto a siliconized polyester film protective layer to be removed before use, in a thickness such that, after the removal of the solvent, a weight of the coating of about 80 g/m$^2$ results. After the removal of the solvent, the dried film is laminated with a thin polyester film (back layer of the TTS), and the finished TTS are stamped out of the complete laminate.

Example 2 (Formulation 3)

5.0 g of fentanyl, 15.0 g of polypinene, 10.0 g of glycerol, 15.0 g of dioctylcyclohexane and 110 g of the adhesive solution having a solids content of 50.0% are combined and stirred until the fentanyl has dissolved.

The resulting material is coated using a doctor blade onto a siliconized polyester film (protective layer to be removed before use) in a thickness such that, after the removal of the solvent, a weight of the coating of about 80 g/m$^2$ results. After the removal of the solvent, the dried film is laminated with a thin polyester film (back layer of the TTS) and the finished TTS are stamped out of the complete laminate.

The invention claimed is:

1. A transdermal therapeutic system (TTS) consisting of:
   A) an active compound-impermeable back layer;
   B) one matrix layer based on polyacrylate and comprising fentanyl; and
   C) a protective film to be removed before use;
   wherein said polyacrylate:
   i) is self-adhesive;
   ii) is free of carboxyl groups, but has at least one hydroxyl group;
   iii) is prepared from a monomer mixture consisting of:
      a) esters of acrylic and/or methacrylic acid, which are esters of alcohols having 1 to 8 carbon atoms; and
      b) 2-hydroxyethyl acrylate or 2-hydroxyethyl methacrylate in amounts of up to 20% by weight; and
   iv) has a saturation solubility for fentanyl of between 5 and 20 percent by weight; and
   wherein said one matrix layer contains at least 80 percent by weight of the incorporated fentanyl in molecularly disperse dissolved form.

2. The transdermal therapeutic system (TTS) according to claim 1, wherein the esters of acrylic and/or methacrylic acid according to iii a) are selected from the group consisting of 2-ethylhexyl acrylate, n-octyl acrylate, propyl acrylate, n-butyl acrylate, iso-butyl acrylate and the corresponding methacrylates.

3. The transdermal therapeutic system (TTS) according to claim 1, wherein the fentanyl is present in a concentration of at least 5% by weight in the matrix layer.

4. The transdermal therapeutic system (TTS) according to claim 1, wherein the fentanyl is present in a concentration of at most 20% by weight in the matrix layer.

5. The transdermal therapeutic system (TTS) according to claim 1, wherein the fentanyl is completely dissolved in molecularly disperse form in said polyacrylate.

6. The transdermal therapeutic system (TTS) according to claim 1, wherein the polyacrylate contains free hydroxyl groups that are crosslinked by $Al^{3+}$ or $Ti^{4+}$.

7. The transdermal therapeutic system (TTS) according to claim 1, wherein the polyacrylate has a saturation solubility for fentanyl of between 5 and 12 percent by weight.

8. The transdermal therapeutic system (TTS) according to claim 7, wherein the polyacrylate has a saturation solubility for fentanyl of between 5 and 10 percent by weight.

9. The transdermal therapeutic system (TTS) according to claim 1, wherein said one matrix layer contain at least one substance which improves the permeation rate through human skin, said substance being selected from the group consisting of glycols, fatty acids, fatty acid esters, fatty alcohols and glycerol esters.

10. The transdermal therapeutic system (TTS) according to claim 1, wherein said one matrix layer contains at least one substance which lowers the solubility of the active compound, said substance being selected from the group consisting of liquid hydrocarbons, liquid paraffin, hydrocarbon resins, polar substances and polyethylene glycols having a molecular weight from 200 to 1000.

11. The transdermal therapeutic system (TTS) according to claim 1, wherein the esters of acrylic and/or methacrylic acid according to iii a) are selected from the group consisting of 2-ethylhexyl acrylate, n-octyl acrylate, propyl acrylate, n-butyl acrylate, iso-butyl acrylate and the corresponding methacrylates;
wherein the polyacrylate contains free hydroxyl groups that are crosslinked by $Al^{3+}$ or $Ti^{4+}$;
wherein fentanyl is completely dissolved in molecularly disperse form in said polyacrylate;
wherein the one matrix layer contains at least one substance which improves the permeation rate through human skin, said substance being selected from the group consisting of glycols, fatty acids, fatty acid esters, fatty alcohols and glycerol esters; and
wherein the one matrix layer contains at least one substance which lower the solubility of the active compound, said substance being selected from the group consisting of liquid hydrocarbons, liquid paraffin, hydrocarbon resins, polar substances and polyethylene glycols having a molecular weight from 200 to 1000.

12. A transdermal therapeutic system (TTS) consisting of:
A) an active compound-impermeable back layer;
B) at least one matrix layer based on polyacrylate and comprising fentanyl; and
C) a protective film to be removed before use;
wherein said polyacrylate:
i) is self-adhesive;
ii) is free of carboxyl groups, but has hydroxyl groups to effect crosslinking;
iii) is prepared from a monomer mixture consisting of:
a) esters of acrylic and/or methacrylic acid, which are esters of alcohols having 1 to 8 carbon atoms; and
b) 2-hydroxyethyl acrylate and/or 2-hydroxyethylmethacrylate;
wherein each monomer is present in the monomer mixture; and
iv) has a saturation solubility for fentanyl of between 5 and 20 percent by weight;
wherein said at least one matrix layer contains at least 80 percent by weight of the incorporated fentanyl in molecularly disperse dissolved form;
wherein the amount of 2-hydroxyethyl acrylate and/or 2-hydroxyethylmethacrylate is up to 20% by weight; and
wherein said polyacrylate is crosslinked by polyvalent cations that are selected from the group consisting of $Al^{3+}$ or $Ti^{4+}$.

13. The transdermal therapeutic system (TTS) according to claim 12, wherein the polyacrylate has a saturation solubility for fentanyl of between 5 and 12 percent by weight.

14. The transdermal therapeutic system (TTS) according to claim 13, wherein the polyacrylate has a saturation solubility for fentanyl of between 5 and 10 percent by weight.

15. The transdermal therapeutic system (TTS) according to claim 12, wherein said at least one matrix layer contains at least one substance which lowers the solubility of fentanyl, said substance being selected from the group consisting of liquid hydrocarbons, liquid paraffin, hydrocarbon resins, polar substances and polyethylene glycols having a molecular weight from 200 to 1000.

16. The transdermal therapeutic system (TTS) according to claim 13, wherein said at least one matrix layer contains at least one substance which lowers the solubility of fentanyl, said substance being selected from the group consisting of liquid hydrocarbons, liquid paraffin, hydrocarbon resins, polar substances and polyethylene glycols having a molecular weight from 200 to 1000.

17. The transdermal therapeutic system (TTS) according to claim 14, wherein said at least one matrix layer contains at least one substance which lowers the solubility of fentanyl, said substance being selected from the group consisting of liquid hydrocarbons, liquid paraffin, hydrocarbon resins, polar substances and polyethylene glycols having a molecular weight from 200 to 1000.

* * * * *